(12) United States Patent
Boucher et al.

(10) Patent No.: US 6,279,326 B1
(45) Date of Patent: Aug. 28, 2001

(54) TRANSPORTABLE DEVICE FOR STORING AND SUPPLYING CRYOGENIC FLUID, MORE PARTICULARLY MEDICAL OXYGEN

(75) Inventors: Guillaume Boucher, Nogent sur Marne; Herve Bertarione, Meounes les Montrieux, both of (FR)

(73) Assignee: L'Air Liquide, Societe Anonyme pour l'Etude et l'Exploitation des Procedes Georges Claude, Paris (FR)

( * ) Notice: Subject to any disclaimer, the term of this patent is extended or adjusted under 35 U.S.C. 154(b) by 0 days.

(21) Appl. No.: 09/494,511

(22) Filed: Jan. 31, 2000

(30) Foreign Application Priority Data

Oct. 29, 1999 (FR) .................................................. 99 13617
Nov. 23, 1999 (FR) .................................................. 99 14730

(51) Int. Cl.⁷ ..................................................... F17C 9/02
(52) U.S. Cl. .......................................... 62/48.1; 62/50.2
(58) Field of Search ................................. 62/48.1, 50.2, 62/285

(56) References Cited

U.S. PATENT DOCUMENTS

| 1,417,292 | * | 5/1922 | Andrews | 62/50.2 |
| 1,464,319 | * | 8/1923 | Heylandt | 62/50.2 |
| 2,454,934 | * | 11/1948 | Mathis et al. | 62/48.1 |
| 3,199,303 | | 8/1965 | Haumann et al. | |
| 3,260,060 | * | 7/1966 | Pauliukonis et al. | 62/48.1 |
| 4,211,086 | * | 7/1980 | Leonard et al. | 62/48.1 |
| 4,716,738 | * | 1/1988 | Tatge et al. | 62/50.2 |

FOREIGN PATENT DOCUMENTS 05041   6/1915  (GB) .

* cited by examiner

*Primary Examiner*—William Doerrler
(74) *Attorney, Agent, or Firm*—Young & Thompson

(57) ABSTRACT

A reservoir of the device supports, in its upper portion, a profiled flange forming a handling apparatus for the device and a trough to collect and discharge, via an opening, the water of condensation forming on a vaporization coil. The coil has turns of changing diameters, supported by support combs on the trough and enclosed in a cover provided with peripheral and upper air openings. The cover includes an element for securing a receptacle that directly coacts, by gravity, condensates.

22 Claims, 2 Drawing Sheets

TRANSPORTABLE DEVICE FOR STORING AND SUPPLYING CRYOGENIC FLUID, MORE PARTICULARLY MEDICAL OXYGEN

FIELD OF THE INVENTION

The present invention relates to transportable devices for storing and supplying cryogenic fluid, of the type comprising a storage reservoir for the fluid in liquid phase, a supply circuit for the fluid in gaseous phase to at least one user station, arranged on the upper portion of the reservoir and comprising at least one vaporization coil, and handling the device.

BACKGROUND OF THE INVENTION

A device of this type is described in U.S. Pat. No. 4,211,086 (Beatrice Foods Company). In this document, the transport and handling of the device are ensured by pivoted handles fixed on the sidewalls of the reservoir, which does not permit correct nor easy handling by the user. Moreover, the supply circuit for the fluid in gaseous phase is enclosed in a closed housing constituted by the sealed assembly of a cover substantially free from openings and a base with a T-shaped profile welded on the reservoir. Such an arrangement does not permit suitable heat exchange nor the evacuation of water vapor accumulating in the cover, particularly because of the cold vaporization coil.

More recently, there have been proposed analogous devices with a profiled base support for the cover connected by a tube projecting outwardly from the cover to a small bottle suspended laterally from the reservoir and receiving the condensate accumulating in the base, in an inconvenient and hardly optimum arrangement.

SUMMARY OF THE INVENTION

The present invention has for its object to provide an improved device permitting, simply and effectively, at low cost and offering a great versatility, the collection and accumulation with high efficiency of the condensates in the cover whilst greatly facilitating handling of the device and optimizing the performance of the vaporization coil.

To do this, according to one characteristic of the invention, the handling means of the device are at least in part constituted by a profiled flange mounted on the reservoir, forming a trough for the collection and evacuation of the condensate and provided with an outlet opening for the condensate.

According to other characteristics of the invention:
the flange comprises a downwardly curved external portion forming a handrail for gripping and handling, connecting to a central mounting portion on the reservoir by an intermediate upwardly curved portion and provided with at least one hollow radial passage, thereby permitting free circulation of liquid between the central portion and the external portion.
at least one portion of the circuit is sheltered in a pierced cover, comprising typically a lower end in the form of a flared skirt that comes into bearing against the periphery of the flange, thereby enclosing the handrail, the skirt-shaped portion comprising typically angular aeration openings angularly spaced about the cover.
the cover comprises means for attaching a receptacle for collecting condensate, having typically a condensate reception trough extending below the evacuation opening of the flange in the assembled arrangement.
the cryogenic is medical oxygen, typically for home oxygen therapy treatments.

The present invention also relates to devices for vaporizing a cryogenic liquid suitable for transportable storage and supply devices for cryogenic fluid defined above, more particularly atmospheric devices for vaporization and reheating of a cryogenic liquid containing oxygen for oxygen therapy, of the type comprising a coil constituted by several coaxial windings with ordinarily a substantially vertical axis, having a first end connected to a source of cryogenic liquid and a second end connectable to a user circuit, for example for the supply of a respiratory mask.

In known devices of this type, as described in U.S. Pat. No. 4,211,086 mentioned above, the coil comprises superposed windings of substantially constant diameter and of an axial spacing which is also substantially constant. These devices have the drawback that, in use, the condensation of water which inevitably takes place along the coil, is accompanied by the formation of drops of water falling downwardly of the coil, which is to say onto the colder turns, accumulating on these lower turns in the form of layers of ice which greatly reduce the heat exchange performance of the coil and require in practice an increased length, hence an increase in the overall volume. This phenomenon of condensation and deposit of ice is further increased when the coil is enclosed in a cover capping the cryogenic gas reservoir constituting said source.

The present invention also has for its object to provide a simple vaporization device, which will be reliable and inexpensive, eliminating the above problems and permitting guaranteeing, in a compact form easily disposable in an envelope, by a vaporization output that is substantially constant with time.

To do this, according to one characteristic of the invention, at least the two lower turns of the coil have a greater diameter than the other turns.

BRIEF DESCRIPTION OF THE DRAWINGS

Other characteristics and advantages of the invention will become apparent from the following description of one embodiment, given by way of non-limiting example, with respect to the accompanying drawings, in which.

DETAILED DESCRIPTION OF PREFERRED EMBODIMENTS

Figure 1:
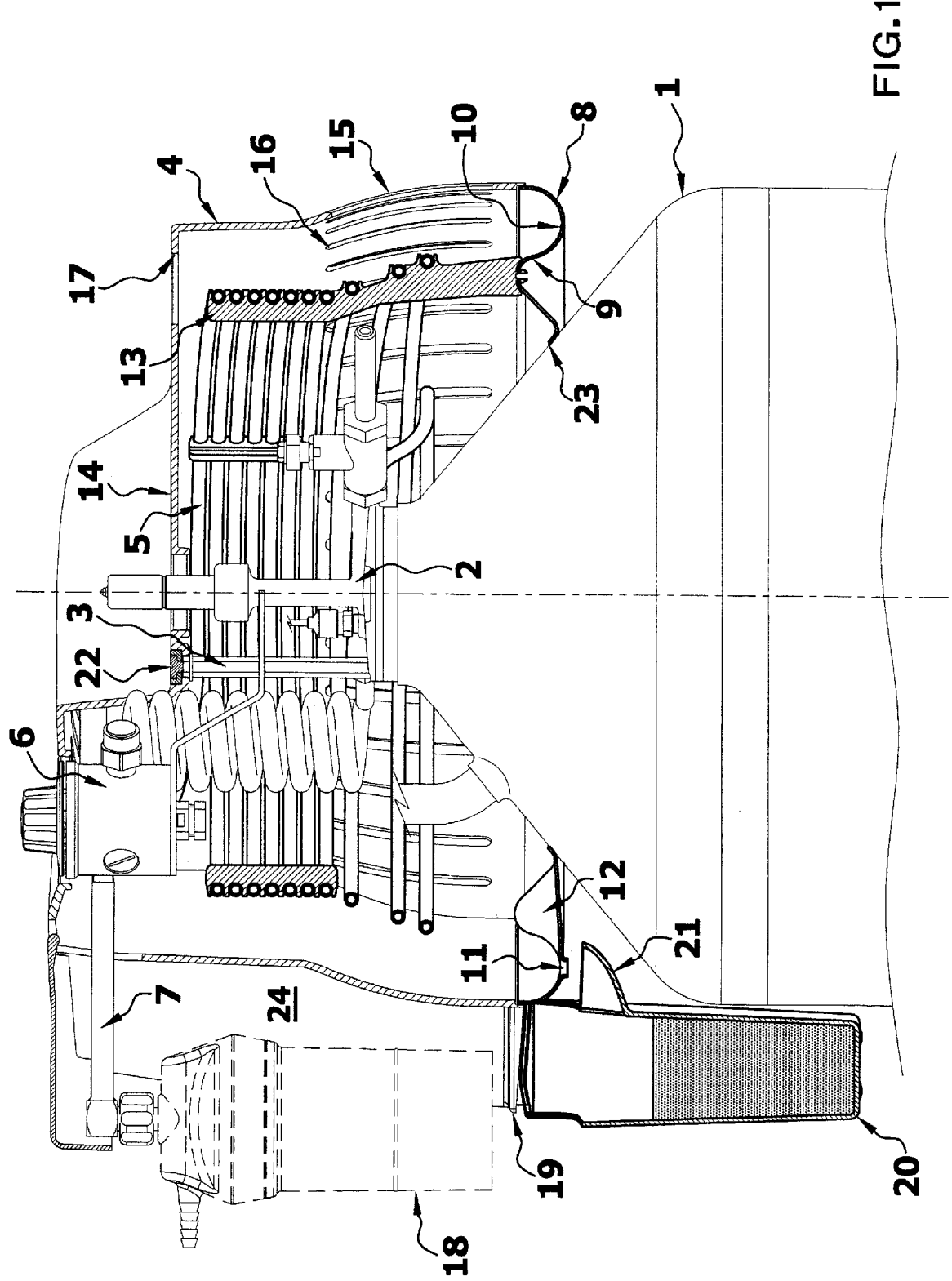
FIG. 1 is a fragmentary cross-sectional schematic view, of the upper portion of a device according to the invention.

In the drawings, there will be seen the upper conical portion of a reservoir 1 for cryogenic liquid under pressure, typically liquid oxygen, with a vertical axis.

At its upper end, the reservoir comprises a filling and withdrawing head 2 for gas, comprising particularly a vertical securement rod 3, with a screw 22, a cover or cap 4, as will be further seen. To the head 2 is connected the upstream end 31 of a vaporization coil 5, preferably coaxial with the reservoir 1 and whose downstream end 32 is connected, via a valve/expander block 6, to a gas outlet 7 for connection to a user circuit, typically a breathing circuit of a patient (not shown). Preferably, as will be seen later, at least the base of the coil 5 comprises windings that are spaced axially farther one from another than the upper windings and of a diameter increasing downwardly, to prevent icing by the drops of condensation water appearing on the least cold turns of the coil and dripping downwardly by gravity.

According to one aspect of the invention, these drops of condensation are collected in an angular flange structure, generally indicated by the reference 8, welded at its central portion on the conical wall 23 of the reservoir 1 and having, in transverse cross-section, from this central portion, a profile forming successively an upwardly curved region 9 then a peripheral downwardly curved region 10 forming a circular gripping handrail, the hollow of the curved portion 9 permitting receiving the fingers of the hand of the handler. At one point on the handrail there is provided, in the bottom of the peripheral curved portion 10, a drain opening 11 permitting evacuating by gravity the condensed water collected in the flange 8. The opening 11 is preferably formed at the lowest point of the flange 8 which has, for this purpose, a slight declivity in the direction toward the opening 11. A substantial portion of the condensates dripping into the central portion of the flange 8, there is provided at least at the level of the opening 11, at least one radial valley 12 locally interrupting the intermediate curved portion 9 to permit free communication of the liquid on opposite sides of this latter.

In a preferred embodiment, as shown, the coil 5 is supported by support combs 13 typically of plastic material, whose lower portion is mounted preferably by simple clipping on the intermediate curved portion 9, provided typically, in its upper portion, with openings for this purpose.

According to one aspect of the invention, the cover 4 comprises an upper transverse wall 14 serving for the securement of the cover 4 on the reservoir 1 via the vertical pillar 3, and the peripheral portion in the form of a downwardly flared skirt 15 whose lower edge bears on the peripheral edge of the curved portion 10 of the flange 8. To cause atmospheric vaporization with optimum heat exchange, the skirt 15 comprises, typically over most of its perimeter, a series of vertical parallel slots 16 and the upper wall 14 comprises, adjacent its periphery, a series of radial slots 17.

According to one aspect of the invention, the cover 4 forms laterally a housing defining a recess 24 to receive at least a portion of a humidifying receptacle indicated in broken lines at 18, which connects to the outlet channel 7. Preferably, the recess 24 comprises at its base means 19 for demountable securement, preferably of the type with a slide, of a removal receptacle 20 for receiving condensate, comprising a trough 21 extending, in the attached position of the receptacle 20, below the outlet opening 11.

The cover 4 and the receptacle 20 are preferably made of a rigid plastic material. The reservoir 1 preferably comprises, at its base, rollers facilitating its movement.

Figure 2:
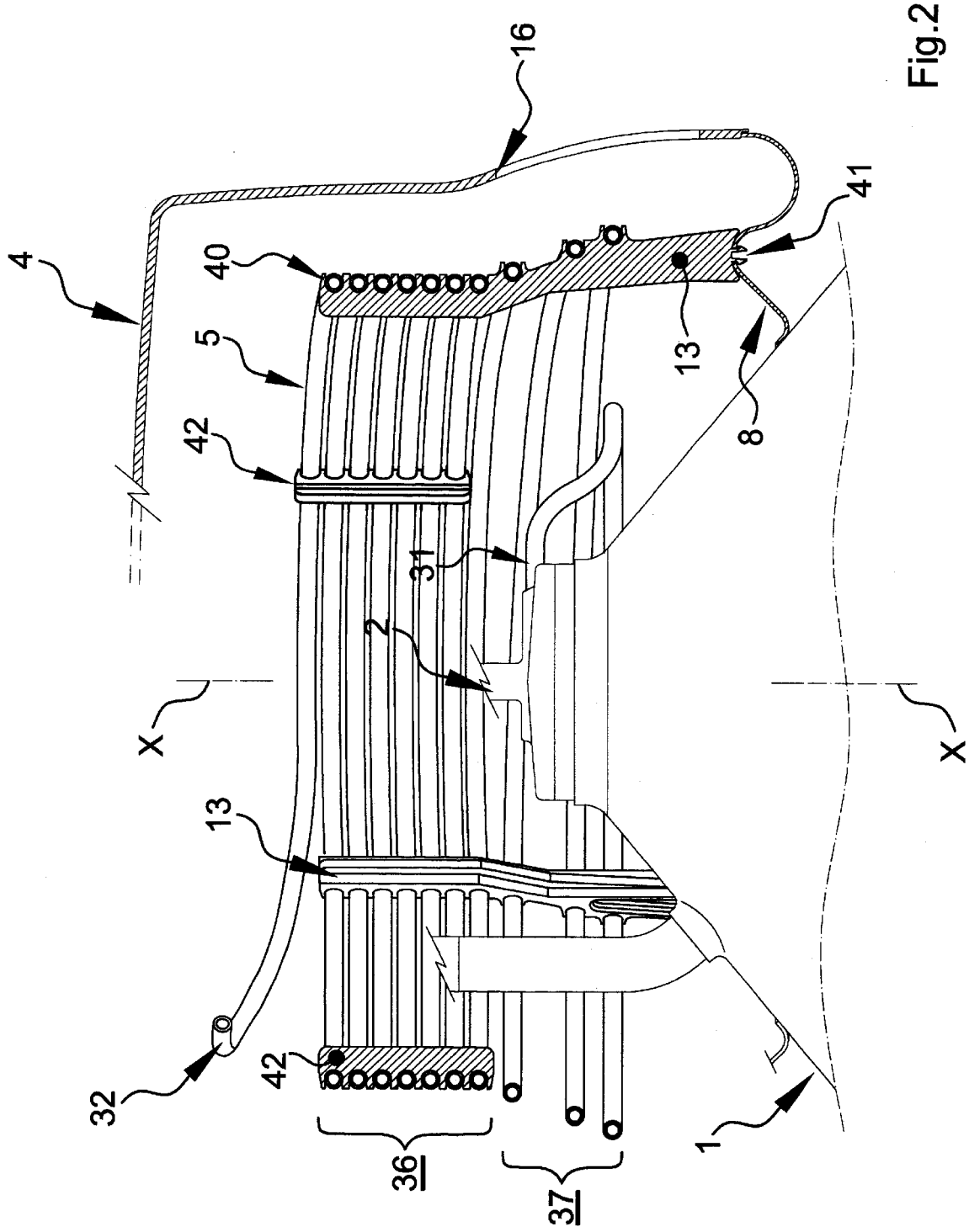
FIG. 2 shows on a larger scale a vaporization coil according to the invention.

As is better seen in FIG. 2, the coil 5, constituted by winding a metal tube which is a good heat conductor, conventionally of aluminum, on a profile mandrel, is divided into an upper portion 36 comprising at least two, typically six or seven adjacent turns and a substantially constant diameter, and a lower portion 37, partially surrounding the upper end of the reservoir 1, comprising at least two, in practice three or four turns, spaced farther axially one from the other and of downwardly increasing diameters, the lowermost complete turn having the greatest diameter and the uppermost complete turn having a diameter slightly greater than that of the turns of the upper portion 36.

In this way, the drops of water of condensation appearing on the turns that are the least cold of the upper portion 36, flow and drip downwardly without falling, or very little, on the coldest turns of the lower portion 37, to accumulate in the trough formed by the flange 8 from which the water is evacuated toward the condensate collection receptacle 20. Moreover, the axial and radial spacing of the lower turns guarantees a greatly improved heat exchange with the surrounding atmosphere.

Preferably, as mentioned above, the coil 5 is supported by support combs 13 that are angularly spaced, shaped to correspond to the profile of the coil 5, and externally comprising a series of recesses 40 arranged to receive the different turns of the coil 5. The support combs 13, of a material of low heat conductivity, typically of a plastic material, are preferably mounted at their base by clipping 41 in the structure of the flange forming the trough 8. Preferably, the upper turns 36 of the coil 5 are maintained in position, as are the support combs 13, by spacer combs 42 of reduced height.

Although the invention has been described in connection with a particular embodiment, it is not thereby limited but is adaptable for modifications and variations which will be apparent to one skilled in the art, within the scope of the following claims.

What is claimed is:

1. Transportable device for storing and supplying cryogenic fluid, comprising a reservoir for storage of fluids in liquid phase, a supply circuit for fluid in gaseous phase to at least one user station, arranged on the upper portion of the reservoir and comprising at least one vaporization coil, and means for handling the device, wherein the handling means are at least in part constituted by a profiled flange mounted on the reservoir, forming a trough for collecting and discharging condensate and provided with a condensate discharge opening.

2. Device according to claim 1, wherein the flange comprises an external portion that is downwardly curved, forming a handrail connecting a central mounting portion of the flange on the reservoir by an upwardly curved middle portion and provided with at least one hollow radial passage.

3. Device according to claim 2, wherein the coil is supported by support combs mounted on the middle portion of the flange.

4. Device according to claim 1, wherein at least one portion of the fluid supply circuit is shielded in a pierced cover.

5. Device according to claim 4, wherein the cover comprises a lower end portion in the form of a flared skirt that bears against the periphery of the flange.

6. Device according to claim 4, wherein the cover comprises air openings angularly spaced about this skirt.

7. Device according to claim 4, wherein the cover comprises means for securing a receptacle for collecting condensate.

8. Device according to claim 7, wherein the receptacle comprises a trough for reception of condensate, extending in secured configuration below the discharge opening of the flange.

9. Device according to claim 4, wherein the cover comprises a lateral recess to receive at least in part a humidifying receptacle insertable in the outlet of the fluid supply circuit.

10. Device according to claim 1, wherein the coil comprises turns of different diameters.

11. Device for the vaporization of a cryogenic fluid for a transportable device for storing and supplying cryogenic fluid, comprising at least one reservoir, comprising a coil constituted of several coaxial turns about a substantially vertical axis, having a first end in connection with the reservoir of cryogenic fluid and a second end connectable to a user circuit, wherein at least two of the lower turns of the coil have a larger diameter than the other turns and at least the two upper turns of the coil have a same reduced diameter.

12. Device according to claim 11, wherein at least the two lower turns have a diameter decreasing upwardly.

13. Device according to claim 12, wherein the mean axial distance between the turns is greater for the lower turns than for the upper turns.

14. Device according to claim 11, wherein the coil is disposed in a non-sealed chamber forming a cover for the upper portion of the reservoir.

15. Device according to claim 1, wherein the cryogenic fluid is oxygen.

16. A method of supplying oxygen to a user comprising the step of storing and supplying oxygen in the device according to claim 15.

17. Device according to claim 11, wherein the cryogenic fluid is oxygen.

18. A method of supplying oxygen to a user comprising the step of storing and supplying oxygen in the device according to claim 11.

19. A transportable device for storing and supplying a cryogenic fluid, comprising a reservoir for storing the fluid in liquid phase, a supply circuit for supplying the fluid in gaseous phase to at least one user conduit, arranged on the upper part of the reservoir and comprising at least one vaporization coil having several turns, wherein at least two of the lower turns have a diameter larger than the other turns.

20. The device of claim 19, wherein at least the upper turns of the coil have a same reduced diameter.

21. The device of claim 19, wherein the coil is housed in an apertured cover.

22. The device of claim 21, wherein the cover is mounted on the reservoir via a profiled flange forming an annular trough.

* * * * *